US008307591B2

(12) United States Patent
Steinle et al.

(10) Patent No.: US 8,307,591 B2
(45) Date of Patent: Nov. 13, 2012

(54) EMBEDDING UNIT FOR DISPLAY DEVICES

(75) Inventors: Wolfgang Steinle, München (DE); Nils Frielinghaus, Heimstetten (DE); Christoffer Hamilton, München (DE)

(73) Assignee: Brainlab AG, Feldkirchen (DE)

( * ) Notice: Subject to any disclaimer, the term of this patent is extended or adjusted under 35 U.S.C. 154(b) by 442 days.

(21) Appl. No.: 12/406,982

(22) Filed: Mar. 19, 2009

(65) Prior Publication Data

US 2009/0241437 A1 Oct. 1, 2009

Related U.S. Application Data

(60) Provisional application No. 61/039,127, filed on Mar. 25, 2008.

(30) Foreign Application Priority Data

Mar. 19, 2008 (EP) .................................... 08153020

(51) Int. Cl.
*E04C 2/52* (2006.01)

(52) U.S. Cl. ..................................................... 52/220.1

(58) Field of Classification Search .................. 52/36.4, 52/36.1, 220.8, 220.1
See application file for complete search history.

(56) References Cited

U.S. PATENT DOCUMENTS

| | | | | |
|---|---|---|---|---|
| 5,483,779 | A * | 1/1996 | Crawford et al. | 52/645 |
| 5,537,290 | A | 7/1996 | Brown et al. | |
| 5,778,612 | A * | 7/1998 | Kissinger et al. | 52/205 |
| 6,246,573 | B1 * | 6/2001 | Khan et al. | 361/679.55 |
| 7,417,681 | B2 * | 8/2008 | Lieberman et al. | 348/333.1 |
| 2002/0104271 | A1 * | 8/2002 | Gallant | 52/36.1 |
| 2003/0019165 | A1 | 1/2003 | Gallant et al. | |
| 2004/0046744 | A1 * | 3/2004 | Rafii et al. | 345/168 |
| 2004/0242988 | A1 * | 12/2004 | Niwa et al. | 600/407 |
| 2005/0086871 | A1 * | 4/2005 | MacGregor et al. | 52/36.1 |
| 2005/0268825 | A1 * | 12/2005 | Mueller et al. | 108/60 |
| 2007/0123160 | A1 * | 5/2007 | Mandel et al. | 454/184 |
| 2008/0054144 | A1 | 3/2008 | Wohlford | |

FOREIGN PATENT DOCUMENTS

| | | |
|---|---|---|
| DE | 40 04 200 | 8/1991 |
| DE | 20 2005 014 294 | 12/2005 |
| JP | 2005045336 A * | 2/2005 |
| WO | 02/096335 | 12/2002 |

OTHER PUBLICATIONS

"Suite Dreams . . . are made of this", Brainlab integrated OR solutions, portfolio.

* cited by examiner

*Primary Examiner* — Christine T Cajilig
(74) *Attorney, Agent, or Firm* — Renner, Otto, Boisselle & Sklar, LLP

(57) ABSTRACT

The invention relates to an embedding unit for display devices to be embedded in a building, comprising at least one receptacle for a medical display device.

43 Claims, 3 Drawing Sheets

EMBEDDING UNIT FOR DISPLAY DEVICES

RELATED APPLICATION DATA

This application claims the priority of U.S. Provisional Application No. 61/039,127, filed on Mar. 25, 2008, which is hereby incorporated in its entirety by reference.

FIELD OF THE INVENTION

The invention relates to an embedding unit for display devices to be embedded in a building. In particular, it relates to an embedding unit for medical display devices.

BACKGROUND OF THE INVENTION

Modern operating theatres are now hardly imaginable without medical display devices, with the aid of which operations can be planned, prepared, performed and discussed. These display devices are normally connected to computers on which patient data can be stored, processed and relayed. In professional circles, two ways in which patient data can be displayed are known in principle. On the one hand, computer units which are widely known can be provided; however, they have a large space requirement and therefore take up space which in operating theatres in particular could be used in other ways. Also, a discussion involving several people is extremely difficult in front of a conventional computer monitor. Conventional computer systems are also highly susceptible to contamination and therefore unsuitable for operating theatres. For these reasons, there has recently been an ever-increasing transition to large-format flat screens which are now available and can for example be installed on the walls of the operating theatres. However, it is still not possible for a plurality of the monitors—in particular when they are situated in different rooms—to access the same computer in a way which saves on resources. Also, locations firstly have to be selected for these flat screens, at which they can be fastened to the wall, wherein either a suspension device has to be installed on the wall, or—if the flat screen is to be integrated in the wall—a corresponding recess has to be cut into the wall. This represents a significant effort and cost and not least leads to contamination of the entire operating theatre and the corresponding consequences.

SUMMARY OF THE INVENTION

It is the object of the invention to provide a way of installing a medical display device in a building, in particular in an operating theatre, such that a display device can be installed at the location determined for it in a simple, clean and uncomplicated way.

This object is solved by an embedding unit for display devices to be embedded in a building, comprising at least one receptacle for a medical display device. The sub-claims define the preferred embodiments of the invention.

The embedding unit in accordance with the invention comprises at least one receptacle for a medical display device, wherein the embedding unit is configured to be embedded in a building. In other words, even as the building is being designed and/or built, a suitable location is selected at which the display device is subsequently to be arranged in the operating theatre. It is then possible, even as the building is being built, for a kind of cavity to be provided in the building at said point by the embedding unit, such that the display device can subsequently be embedded in the cavity in a clean and space-saving way. The embedding unit in accordance with the invention can of course also be used for retroactive embedding, i.e. retrofitting in an already existing building.

The wording "to be embedded in a building" is then to be understood such that the embedding and/or embedding location can be at any point within the building. This means that the embedding unit can be embedded in intermediate walls, outer walls, ceilings, floors or similar room-separating elements. In addition, however, it is also conceivable for it to be embedded in other planar elements within the building, such as for instance cupboard walls or doors or room doors.

If the subsequent display device and therefore the embedding unit is provided in parts of the building itself, the building around the positioned embedding unit—in particular, room-separating elements of the building—are then built in the usual way, wherein the room-separating elements of the building can be walls, ceilings or floors of the building.

It is also conceivable for the display device to be arranged in elements which are not directly part of the structure of the building itself. This is the case if a door of the building, in particular a room door, or a wall cupboard, in particular the door of the wall cupboard, is to be fitted with a display device. A cavity is then merely provided in these elements, into which the embedding unit—which subsequently accommodates a display device—can then be inserted in a simple and uncomplicated way. It is then unnecessary to mount the display device directly to these elements, which would cost space. In summary, it may be said that the embedding unit in accordance with the invention can be attached or embedded anywhere in the building where planar elements having a sufficient surface are available. Consequently, it is then also for example possible to consider embedding it in or on a cupboard, even if room-separating elements are discussed in the following.

The resultant space within the embedding unit can then be used to accommodate the medical display device. The cavity advantageously extends over the entire extent of the embedding unit, such that the embedding unit resembles a common door frame or window frame.

In accordance with a preferred embodiment of the invention, the cavity extends through the entire thickness of the room-separating element of the building, such that a kind of window between two rooms is created. Display devices can then advantageously be installed on both sides of the embedding unit, wherein they can be connected to each other, in particular in a simple way via data lines. This is among other things advantageous when both display devices are being used for communication by staff situated in front of the display devices.

It is also conceivable for the embedding unit itself to already comprise input and/or output conduits for signal and data lines. These can already be arranged on the embedding unit such that the corresponding lines and/or cables pass through the room-separating element of the building, i.e. they can be provided in the room-separating element of the building even as the building is being planned and built. It is then possible for the embedding unit itself to provide ports in the manner of plug sockets, into which one or more display devices can be plugged in a simple way. This additionally simplifies installing the display devices, wherein once embedded, the installation as a whole leaves an aesthetic and tidy impression. Said signal lines can then for example lead to a centrally arranged computer or to other stories or remote spaces in which display devices are likewise provided. The same solution is likewise possible for power cables for supplying energy to the display devices.

Since the electronic systems of the display devices usually emit large amounts of heat, input and/or output conduits for fresh air and exhaust air, respectively, can be provided in or on the embedding unit in another preferred embodiment. Thus, it is on the one hand possible to provide a circulation of air between the corresponding operating theatre and the display device through air slits facing into the operating theatre; however, guiding the air in channels within the room-separating element of the building represents a particularly elegant solution, since the corresponding operating theatre is not then charged with an air flow (with the corresponding danger of contamination). Thus, the display devices are advantageously already “rear-ventilated” within the room-separating element of the building.

In some applications, it is desirable for the embedding unit to be configured with the corresponding display devices in a particularly simple way. Thus, a computer unit can be provided in a decentralized way in or on each embedding unit and supplies one or more display devices of the embedding unit with data and can also serve for communication between the two display units. Since room-separating elements of the building usually exhibit more than twice the depth of common flat screens, it is possible to provide display devices facing away from each other on the opposing sides of the embedding unit, i.e. on both surfaces of the room-separating element of the building. Even when two display devices are installed in one embedding unit, there is still enough space between the display devices to arrange a computer unit in.

It is particularly advantageous, in particular in connection with the communication by staff via the display devices in the building, to fit the embedding unit with one or more cameras which record the space in front of the display devices. The staff can then communicate with each other in the manner of video telephony and directly exchange and discuss data and/or images in a simple or economical way. These or other cameras can also be oriented such that they record the surface of the display devices, in order to identify any contaminants on the surface of the screen. If, for example, a test image is shown on the display device, it can be recorded by the camera, wherein contaminants on the surface of the display are identified by differences between the displayed image and the recorded image. In an additional step, this contaminated region can then be marked by the display device itself, such that cleaning staff are for example informed of the contaminated state of the display device.

It is also possible to provide a projection unit on the embedding unit, which for example projects a virtual keyboard or operating panel onto a surface near the display device, wherein in particular in combination with a camera which records the position of the staff, it is possible to operate the display device in a virtual, non-contact way. This is advantageous in particular in sterile conditions in operating theatres. However, it is also possible for the display device itself to be designed in a known way as a “touch screen”, such that the staff operate it via the surface of the display.

In order to protect the display device when it is not being used, a kind of protective roller blind can be provided in or on the embedding unit, which is drawn over the display device when it is in its idle mode, wherein the protective roller blind can additionally comprise cleaning agents which clean the surface of the display as the protective roller blind is moved over it.

The embedding unit can be configured to any size, such that a display device arranged in it does not completely fill the space available, either in its depth and/or in its planar extent. In order to achieve as pleasing an optical exterior as possible, the display device can be oriented in the embedding unit such that it is flush with the corresponding surface of the room-separating element of the building.

The display device can then be any flat screen, including widely known flat screens, although the use of a digital medical light box is advantageous in the aforementioned applications, since it is designed precisely for these applications.

It is also conceivable for the display devices to be mounted to the embedding unit such that they can be pivoted and/or rotated. This enables reflections on the surface of the display due to viewing it obliquely to be avoided, by always orienting the display device such that the staff have a perpendicular direction of view onto the surface of the display. It is however equally conceivable for both a known analogue light box and a digital light box to be arranged in the same embedding unit such that their display surfaces face away from each other, and for this assembly to be able to be pivoted via a rotational device, such that the staff can choose between the digital light box and the analogue light box by pivoting the entire assembly. Another way of protecting the display device, aside from providing a roller blind, is to pivot the display device, i.e. when it is not being used, it can be pivoted such that the surface of the display lies facing away from the operating theatre, in the interior of the embedding unit.

As already indicated above, it is possible to provide only one display device in the embedding unit in accordance with the invention; however, when the embedding unit is optimally arranged in the building, i.e. for example between two operating theatres, it is conceivable to fit two display units facing away from each other, each facing into one operating theatre. In this way, in addition to using a single embedding unit for two display devices, it is possible to distribute resources between two display units, due to them jointly using a single computer unit and its energy supply.

In addition, an operating panel can be arranged on the embedding unit in the form of a keyboard, which enables inputs by the staff.

If there is still space behind the one display unit or between the two display units in the embedding unit, then this can be used for instance in the form of a shelf or wall cupboard. It is thus possible to provide a plurality of storage options and/or compartments with storage space in the embedding unit. The display unit can then be swung open in a similar way to a cupboard door in order to enable staff to access the storage space in the embedding unit. The display unit can then represent a combination lock in the manner of the door of a safe and allow only authorized staff access.

It is also conceivable for ports to be provided on the embedding unit which are oriented facing into the operating theatre, such that it is possible to connect external apparatuses, via the embedding unit, to the display unit situated in the embedding unit or to a computer system connected to it. This can for example be a video output or input, wherein in the extreme case, the embedding unit can provide ports only and not comprise any display devices.

The embedding unit can also be configured as a rigid frame with fixed dimensions, but it is also conceivable for the embedding unit to be variable in its dimensions. Individual segments of the embedding unit can for example be movable relative to each other using a kind of rail system, so that it can for example be universally adapted to different thicknesses of different room-separating elements of the building or used for different formats of display units. It would also be conceivable for individual segments to telescope relative to each other, wherein it is in particular conceivable for the embedding unit to be divided into eight segments, wherein four segments are respectively arranged on each side of the wall and respectively assigned to each other at the median lines of the four sides of the frame of the embedding unit.

It is also possible to fit the embedding unit in accordance with the invention with a scanner or/and a printer, in order to enable staff to directly input and/or output data. Thus, for instance, a scanner can be provided in the peripheral region of the display device, which for example inputs paper documents or x-ray images which are inserted by the staff and then displayed by the display device. Conversely, a printer is also conceivable, for example likewise arranged on the periphery of the display device, which prints out the documents desired by the staff, which can likewise be displayed by the display device.

The invention is not limited only to its use as an embedding unit for medical display devices; rather, it can also be used in other fields, for example when newly building a residential building or hotel, wherein a television or computer monitor is to be arranged in it. As already described above, it is equally conceivable to embed it in a ceiling of a building, the floor or even in a room door or cupboard door.

BRIEF DESCRIPTION OF THE DRAWINGS

The present invention is described in more detail in an embodiment, on the basis of the enclosed figures, wherein it can comprise individual features and any expedient combination of features.

DETAILED DESCRIPTION

Figure 1:
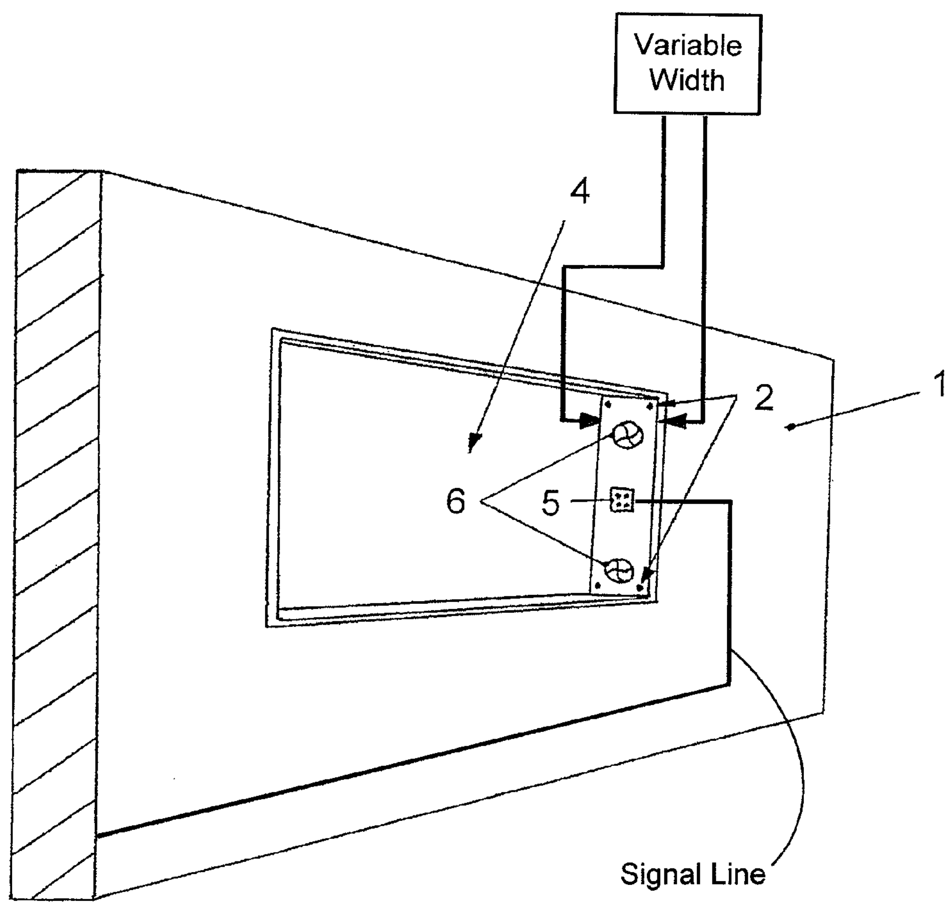
FIG. 1 shows an embedding unit in accordance with the invention, in its embedded state in a wall.

FIG. 1 shows an embedding unit which has already been inserted into and/or embedded in a wall 1 of a building, wherein a kind of rectangular breach and/or cavity 4 is thus created in the wall 1 of the building. The embedding unit comprises a plurality of receptacles 2, at which display devices 3 can subsequently be fastened to the embedding unit. Since in the present case, the embedding unit opens onto both sides, display devices 3 can be inserted into the embedding unit from both rooms bordering the wall 1. Input and/or output devices 5 for signal lines and supplying power, and input and/or output devices 6 for fresh air and exhaust air, respectively, are also provided in the embedding unit. Thus, once inserted into the embedding unit, the display unit 3 is connected to these ports, whereby cables and/or channels to the display device 3 do not have to lead along the wall 1, which would be disruptive and susceptible to contamination. The installation as a whole thus provides an image which is both aesthetically pleasing and insusceptible to contamination and easy to clean.

Figure 2:
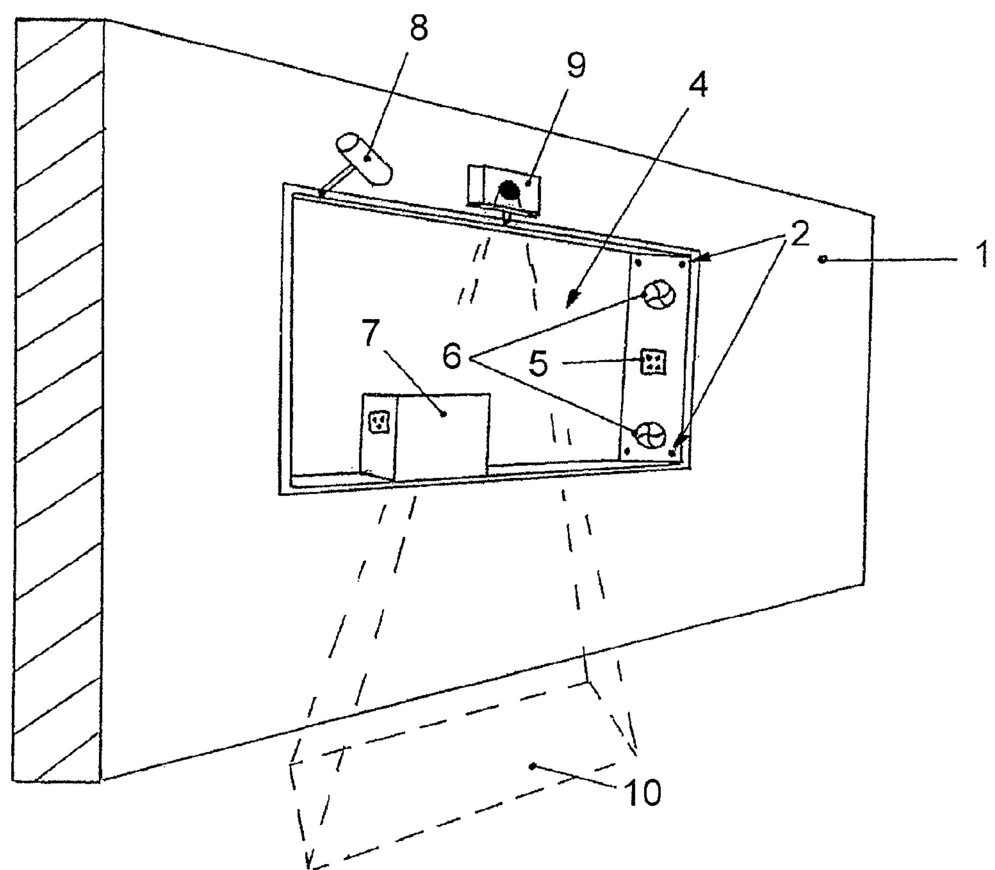
FIG. 2 shows the embedding unit shown in FIG. 1, in combination with a camera, a projector and a computer unit.

In the embodiment shown in FIG. 2, the embedding unit already shown in FIG. 1 has been supplemented by additionally features. Thus, it now also comprises a computer unit which can be connected to the display devices 3 and to the plug socket 5 of the embedding unit, in order to enable data communication both between the display units 3 and to other locations. However, it is also possible for the display units 3 to be connected directly to the plug socket 5.

The embedding unit also comprises a projection unit 9 which projects a virtual keyboard 10 onto the floor in front of the embedding unit and/or the display device 3. Together with the camera 8 arranged on the embedding unit, this enables the staff to operate the display device in a virtual way, since the camera 8 records the environment in front of the embedding unit and/or the display device 3, i.e. also the position and movements of the staff situated in front of the display device 3. A surgeon can then for example work sterilely, since he only operates the display device 3 with his feet and does not have to touch the surface of the display device 3 with his hands.

Figure 3:
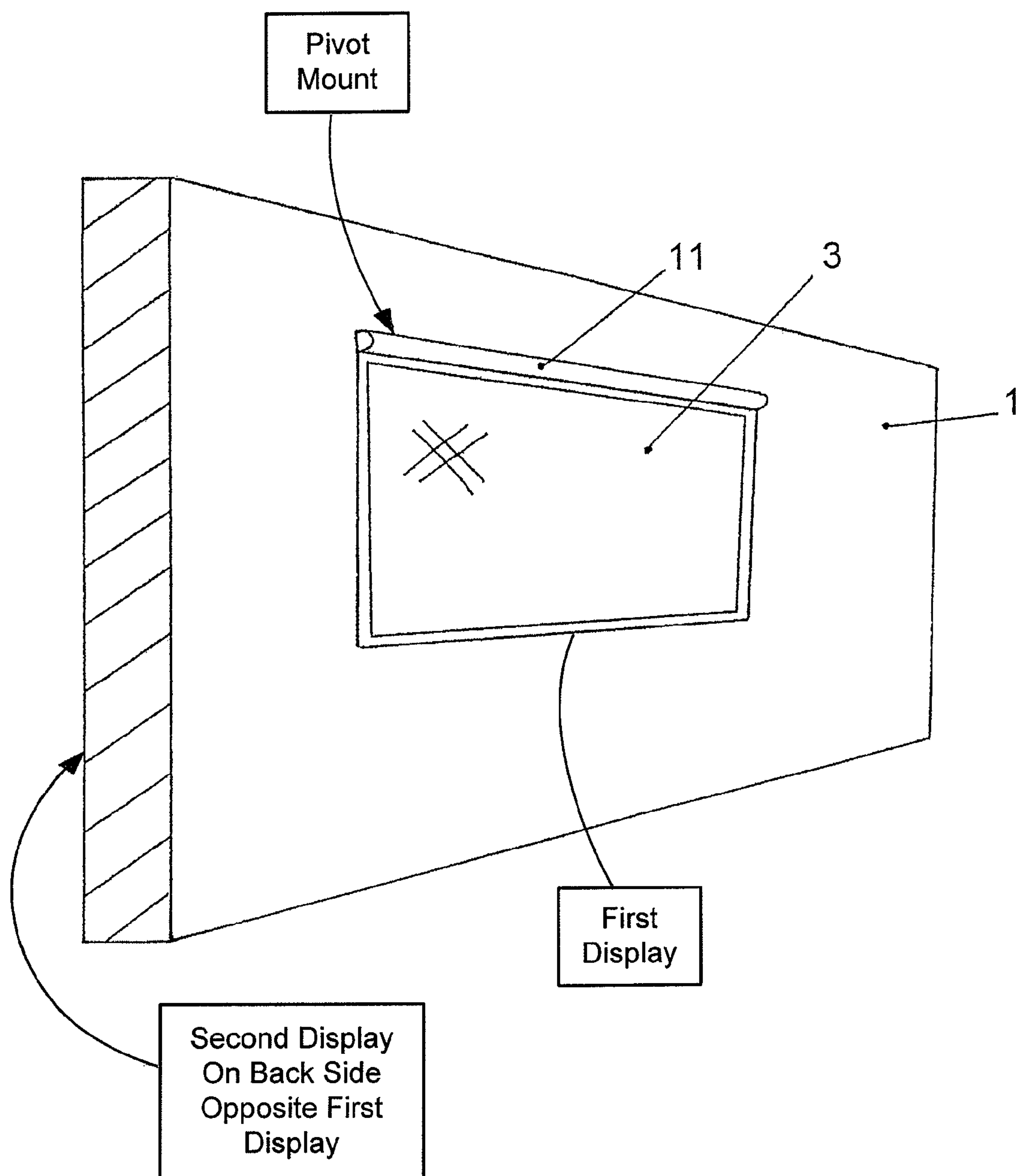
FIG. 3 shows the embedding unit shown in FIG. 1, with a display device inserted.

FIG. 3 shows a display device 3 which has been inserted into the embedding unit and is flush with the surface of the wall 1. All the ports and/or input conduits and/or output conduits of data lines or cooling air channels are situated on the rear side of the display device 3 and pass along the inside of the wall 1. In order to protect the surface of the display, a protective device 11 in the form of a roller blind is arranged above the display device 3. When the display device 3 is not being used or is in an idle mode, this roller blind 11 can be drawn down in front of the display device 3 and thus protects the surface of the display. Cleaning agents on the inner side of the protective device 11 simultaneously clean the surface of the display as the protective device 11 is drawn up and down.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, “code” or a “computer program” embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a “means”) are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. An embedding unit in combination with a room-separating element of a building, the embedding unit being embedded in the room-separating element, the embedding unit comprising:

at least one receptacle mounted in the room-separating element, the receptacle including a front side, a back side and a plurality of lateral sides, the front, back and lateral sides defining an interior space for receiving a medical display device, the front side comprising an opening to the interior space;

at least one input device mounted to a first lateral side of the plurality of lateral sides for causing air to flow into the interior space; and at least one output device mounted to a second lateral side of the plurality of lateral sides for exhausting air from the interior space.

2. The combination according to claim 1, wherein the embedding unit is embedded in a wall of the building.

3. The combination according to claim 1, wherein the embedding unit is embedded in at least one of a ceiling of the building, floor of the building, or a room door.

4. An embedding unit in combination with a room-separating element of a building, the embedding unit being embedded in the room-separating element, the embedding unit comprising:

at least one receptacle mounted in the room-separating element, the receptacle including a front side, a back side and a plurality of lateral sides, the front, back and lateral sides defining an interior space for receiving a medical display device, the front side comprising an opening to the interior space;

at least one input device mounted to a first lateral side of the plurality of lateral sides for causing air to flow into the interior space; and at least one output device mounted to a second lateral side of the plurality of lateral sides for exhausting air from the interior space;

wherein the embedding unit is embedded in the cupboard.

5. The combination according to claim 4, wherein the embedding unit embedded in a cupboard door.

6. The combination according to claim 2, wherein the embedding unit forms a cavity arranged behind the surface of the room-separating element of the building when the embedding unit is inserted into the room-separating element of the building.

7. The combination according to claim 6, wherein the cavity extends over the entire extent of the embedding unit in the plane of the surface of the room-separating element of the building.

8. The combination according to claim 6, wherein the cavity extends through the entire thickness of the room-separating element of the building.

9. The combination according to claim 1, wherein the embedding unit comprises at least one input and/or output device for power supply lines and/or signal lines.

10. The combination according to claim 9, wherein the at least one input and/or output device is arranged between outer surfaces of the room-separating element of the building.

11. The combination according to claim 1, wherein the embedding unit comprises a computer unit.

12. The combination according to claim 11, wherein the computer unit is configured to process data to be displayed by the display device.

13. The combination according to claim 1, wherein the embedding unit comprises a camera which captures at least a part of the space in front of the display device and/or the display device itself.

14. The combination according to claim 1, wherein the embedding unit comprises a projection unit which projects an operating panel in the vicinity of the display device.

15. The combination according to claim 14, wherein the operating panel is a virtual keyboard.

16. The combination according to claim 14, wherein the projection unit projects the operating panel onto the floor situated in the region of the display device.

17. The combination according to claim 1, wherein the embedding unit comprises a protective device for protecting the display device.

18. The combination according to claim 17, wherein the protective device for the display device is a protective roller blind configured to be drawn in front of the display device.

19. The combination according to claim 18, wherein the protective roller blind is configured to wipe the surface of the display of the display device as it is drawn in front of the display device.

20. The combination according to claim 1, wherein the embedding unit is configured as a substantially cuboid shape.

21. The combination according to claim 1, wherein the embedding unit is configured to exhibit substantially the same extension as a display device in the plane of a room-separating element of the building.

22. The combination according to claim 1, wherein the embedding unit is flush with at least one surface of a room-separating element of the building.

23. The combination according to claim 22, further comprising a display device arranged on the embedding unit, wherein the display device is flush with at least one surface of the room-separating element of the building.

24. The combination according to claim 1, further comprising a display device, wherein the display device is a digital medical display device.

25. The combination according to claim 1, further comprising a mount for mounting the display device to the embedding unit, the mount configured to enable rotation or pivoting of the display device relative to the embedding unit.

26. The combination according to claim 25, further comprising the display device, wherein the display device comprises a digital medical display device and an analogue medical display device.

27. The combination according to claim 26, wherein the analogue medical display device faces away from the digital medical display device.

28. The combination according to claim 26, wherein the digital medical display device and the analogue medical display device are configured to pivot and/or rotate relative to the embedding unit.

29. The combination according to claim 25, wherein the display device is configured to pivot and/or rotate into an idle position facing away from a user.

30. The combination according to claim 1, wherein the embedding unit comprises at least one display device.

31. The combination according to claim 30, wherein the embedding unit comprises two display devices.

32. The combination according to claim 30, wherein the at least one display device comprises at least two display devices, and the at least two display devices are respectively arranged on the opposing surfaces of a room-separating element of the building.

33. The combination according to claim 1, wherein the embedding unit comprises an operating panel.

34. The combination according to claim 33, wherein the operating panel is a keyboard.

35. The combination according to claim 1, further comprising a display device and at least one signaling connection operatively coupled to a computer unit, wherein the display device is connected to the signaling connection.

36. The combination according to claim 35, wherein the display device is connected to another of the at least one signaling connections, the another signaling connection operatively coupled to other display devices via the computer unit.

37. The combination according to claim 1, further comprising the display device and a computer unit, wherein the display device and/or the computer unit is connected to external systems via at least one signal line.

38. The combination according to claim 37, wherein the signal line is a signal line arranged in the room-separating element of the building.

39. The embedding unit according to claim 1, further comprising a storage container, the storage container arranged in a volume within the embedding unit.

40. The combination according to claim 1, wherein the embedding unit comprises a video output.

41. The combination according to claim 1, wherein the embedding unit exhibits a variable width, in order to be able to be adapted to different embedding thicknesses.

42. The combination according to claim 1, wherein the first lateral side and the second lateral side are the same lateral side.

43. The combination according to claim 1, wherein the embedding unit comprises one or more ports on a front side facing into an operating theatre to connect to external apparatuses.

* * * * *